United States Patent
Kong

(10) Patent No.: US 12,139,717 B2
(45) Date of Patent: Nov. 12, 2024

(54) IMPROVING PLANT REGENERATION

(71) Applicant: KWS SAAT SE & Co. KGaA, Einbeck (DE)

(72) Inventor: Jixiang Kong, Einbeck (DE)

(73) Assignee: KWS SAAT SE & Co. KGaA, Einbeck (DE)

( * ) Notice: Subject to any disclaimer, the term of this patent is extended or adjusted under 35 U.S.C. 154(b) by 413 days.

(21) Appl. No.: 17/434,516

(22) PCT Filed: Mar. 12, 2020

(86) PCT No.: PCT/EP2020/056743
§ 371 (c)(1),
(2) Date: Aug. 27, 2021

(87) PCT Pub. No.: WO2020/182971
PCT Pub. Date: Sep. 17, 2020

(65) Prior Publication Data
US 2022/0056461 A1    Feb. 24, 2022

(30) Foreign Application Priority Data

Mar. 12, 2019   (EP) .................... 19162189

(51) Int. Cl.
C12N 15/82    (2006.01)
C12N 5/04     (2006.01)

(52) U.S. Cl.
CPC ........... *C12N 15/8201* (2013.01); *C12N 5/04* (2013.01); *C12N 2500/30* (2013.01)

(58) Field of Classification Search
None
See application file for complete search history.

(56) References Cited

U.S. PATENT DOCUMENTS

| | | | |
|---|---|---|---|
| 2003/0093829 A1 | 5/2003 | Chen et al. | |
| 2004/0237133 A1 | 11/2004 | Goldman et al. | |

FOREIGN PATENT DOCUMENTS

| | | | |
|---|---|---|---|
| CN | 103597082 A | | 2/2014 |
| WO | 94/18313 A1 | | 8/1994 |
| WO | 95/09233 A1 | | 4/1995 |
| WO | 03/004659 | | 1/2003 |
| WO | 03/080809 | | 10/2003 |
| WO | 2006/128707 | | 12/2006 |
| WO | 2010/079430 | | 7/2010 |
| WO | 2011/072246 | | 6/2011 |
| WO | 2011/146121 A1 | | 11/2011 |
| WO | 2011/154393 | | 12/2011 |
| WO | 2012/001527 | | 1/2012 |
| WO | 2012/093833 | | 7/2012 |
| WO | 2012/104729 A1 | | 8/2012 |
| WO | 2012/138927 | | 10/2012 |
| WO | 2012/138939 A1 | | 10/2012 |
| WO | 2012/0168124 A1 | | 12/2012 |
| WO | 2016/021973 A1 | | 2/2016 |
| WO | 2018/138385 A1 | | 8/2018 |
| WO | 2019/134884 A1 | | 7/2019 |

OTHER PUBLICATIONS

Poretska, Olena, et al. "The small molecule hyperphyllin enhances leaf formation rate and mimics shoot meristem integrity defects associated with AMP1 deficiency." Plant physiology 171.2 (2016): 1277-1290. (Year: 2016).*
Mao, Yanfei, et al. "Application of the CRISPR—Cas system for efficient genome engineering in plants." Molecular plant 6.6 (2013): 2008-2011. (Year: 2013).*
Zhang, Fei, et al. "Rapid and efficient CRISPR/Cas9 gene editing in Citrus using the YAO promoter." Plant Cell Reports 36 (2017): 1883-1887. (Year: 2017).*
Qifa, Zheng, et al. "Transformation of the Shatian pummelo (Citrus grandis) with the synthetic oak silkworm antibacterial peptide D gene." Hua nan Nong ye da xue xue bao= Journal of South China Agricultural University 20.1 (1999): 103-107. (Year: 1999).*
National Center for Biotechnology Information (2023). PubChem Compound Summary for CID 1486, 2,4-Dichlorophenoxyacetic acid. Retrieved Dec. 8, 2023 from https://pubchem.ncbi.nlm.nih.gov/compound/2_4-Dichlorophenoxyacetic-acid. (Year: 2023).*
National Center for Biotechnology Information (2023). PubChem Compound Summary for CID 768006, n-(4-Amino-2-chlorophenyl)-2,4-dichlorobenzamide. Retrieved Dec. 8, 2023 from https://pubchem.ncbi.nlm.nih.gov/compound/n-_4-Amino-2-chlorophenyl_-2_4-dichlorobenzamide. (Year: 2023).*
Germanà, M. A., et al. "Anther culture in Citrus clementina: a way to regenerate tri-haploids." Australian Journal of Agricultural Research 56.8 (2005): 839-845. (Year: 2005).*
Chemicool Dictionary, Definition of a Derivative, Accessed Dec. 7, 2023 (Year: 2023).*
Alonso, José M., et al. "Genome-wide insertional mutagenesis of Arabidopsis thaliana." Science 301.5633 (2003): 653-657. (Year: 2003).*
Tao, Huang, et al. "Plant regeneration from leaf-derived callus in Citrus grandis (pummelo): Effects of auxins in callus induction medium." Plant Cell, Tissue and Organ Culture 69 (2002): 141-146. (Year: 2002).*
Ivic-Haymes et al., "Identification of highly regenerative plants within sugar beet (Beta vulgaris L.) breeding lines for molecular breeding", In Vitro Cellular and Developmental Biology-Plant, 2005, vol. 41, No. 4, pp. 483-488.

(Continued)

*Primary Examiner* — Weihua Fan
*Assistant Examiner* — Brian James Sullivan
(74) *Attorney, Agent, or Firm* — Troutman Pepper Hamilton Sanders LLP

(57) ABSTRACT

The present invention relates to the field of plant breeding and in particular to the regeneration of plants from cells and other tissues. More particularly, the invention provides methods and means for improving callus and shoot formation and regeneration of plants using hyperphyllin or derivatives thereof.

Figure 1:
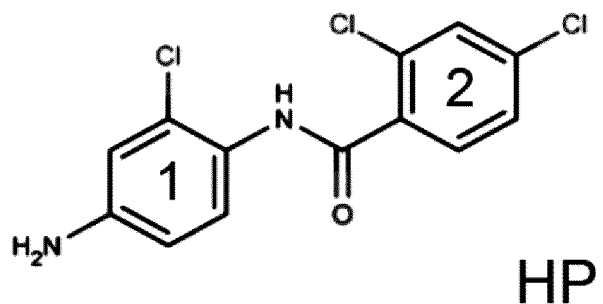
Figure 1:
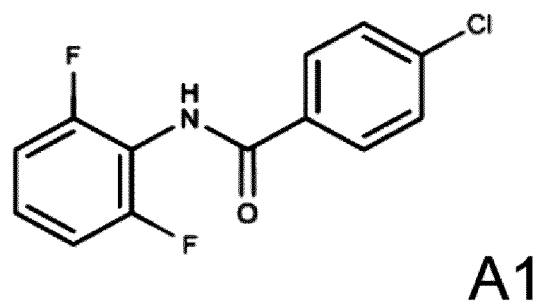
Figure 1:
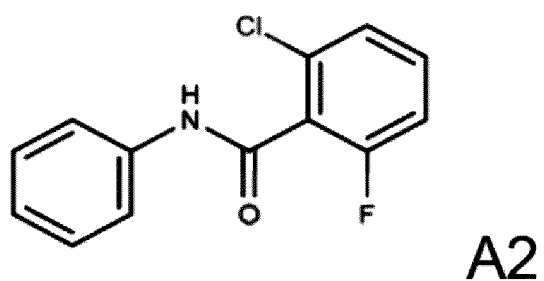
Figure 1:
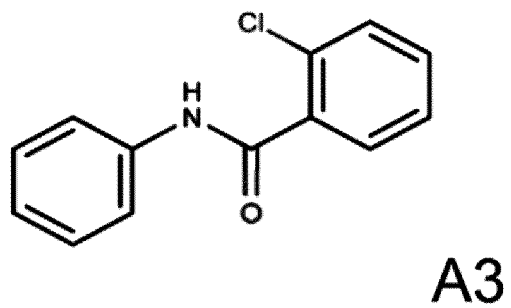

14 Claims, 10 Drawing Sheets
Specification includes a Sequence Listing.

(56) References Cited

OTHER PUBLICATIONS

Tomita et al., "Evaluation of the potential for somatic embryogenesis in sugar beet (Beta vulgaris L.) breeding lines and improvement of regeneration efficiency", Plant Biotechnology, 2013, vol. 30, No. 5, pp. 479-487.
Kishchenko et al., "Production of transgenetic sugarbeet (Beta vulgaris L.) plants resistant to phosphinothricin", Cell Biology International, 2005, vol. 29, No. 1, 2015, pp. 15-19.
Chaudhury et al., "amp1—a mutant with high cytokinin levels and altered embryonic pattern, faster vegetative growth, constitutive photomorphogenesis and precocious flowering", The Plant Journal, 1993, vol. 4, No. 6, pp. 907-916.
Mishutkina et al., "Sugar beet (Beta vulgaris L.) morphogenesis in vitro: effects of phytohormone type and concentration in the culture medium, type of explants, and plant genotype on shoot regeneration frequency", Russian Journal of Genetics, 2006, vol. 42, vol. 2, pp. 150-157.
Helliwell et al., "The Arabidopsis AMP1 gene encodes a putative glutamate carboxypeptidase." The Plant Cell, 2001, vol. 13, No. 9, pp. 2115-2125.
Vidaurre et al., "AMP1 and MP antagonistically regulate embryo and meristem development in Arabidopsis", Development, 2007, vol. 134, No. 14, pp. 2561-2567.
Mordhorst et al., "Somatic embryogenesis in *Arabidopsis thaliana* is facilitated by mutations in genes repressing meristematic cell divisions", Genetics, 1998, vol. 149, No. 2, pp. 549-563.
Poretska et al., "The small molecule hyperphyllin enhances leaf formation rate and mimics shoot meristem integrity defects associated with AMP1 deficiency", Plant Physiology, 2016, vol. 171, pp. 1277-1290.
Ishida et al., "Agrobacterium-mediated transformation of maize", Nature Protocols, 2007, vol. 2, No. 7, pp. 1614-1621.
Isalan et al., "A rapid, generally applicable method to engineer zinc fingers Illustrated by targeting the HIV-1 promoter", Nature Biotechnology, 2001, vol. 19, No. 7, pp. 656-660.
Liu et al. "Design of polydactyl zinc-finger proteins for unique addressing within complex genomes", Proceedings of the National Academy of Sciences, 1997, vol. 94, No. 11, pp. 5525-5530.
Boch et al., "Breaking the code of DNA binding specificity of TAL-type III effectors", Science, 2009, vol. 326, No. 5959, pp. 1509-1512.
Moscou et al., "A simple cipher governs DNA recognition by TAL effectors", Science, 2009, vol. 326, No. 5959, p. 1501.
Zetsche et al., "Cpf1 Is a Single RNA-Guided Endonuclease of a Class 2 CRISPR-Cas System", Cell, 2015, vol. 163, pp. 759-771.
Jinek et al., "A programmable dual-RNA-guided DNA endonuclease in adaptive bacterial immunity", Science, 2012, vol. 337, No. 6096, pp. 816-821.
Burstein et al., "New CRISPR-Cas systems from uncultivated microbes", Nature, 2017, vol. 542, pp. 237-241.
Jore et al., "Structural basis for CRISPR RNA-guided DNA recognition by Cascade", Nature Structural & Molecular Biology, 2011, vol. 18, No. 5, pp. 529-536.
Gaudelli et al., "Programmable base editing of A•T to G•C in genomic DNA without DNA cleavage", Nature, 2017, vol. 551, No. 7681, p. 464.
International Search Report and Written Opinion issued in PCT/EP2020/056743 dated Apr. 15, 2020.
Yang et al., "Altered Meristem Program1 Restricts Shoot Meristem Proliferation and Regeneration by Limiting HD-ZIP III-Mediated Expression of RAP2.6L", Plant Physiology, 2018, vol. 177, No. 4, pp. 1580-1594.
Wu et al., "Establishment of Tissue Culture and Plant Regeneration System of Sugar beet", Sugar Crops of China, 2018, vol. 40 No. 6, pp. 14-18. (with English Abstract and listed in Office Action issued in CN 202080019583 dated Aug. 31, 2023).
Office Action Issued in CN 202080019583 dated Aug. 31, 2023 and English translation.

\* cited by examiner

HP

A1

A2

A3

A

Genotype A:
CIM + 2 ml/L DMSO

Genotype A:
CIM + 2 ml/L DMSO
+ 30 µM HP

Genotype A:
CIM + 2 ml/L DMSO

Genotype A:
CIM + 2 ml/L DMSO
+ 50 µM HP

Genotype A:

Genotype C: Genotype A:

SEQUENCE LISTING

<160> NUMBER OF SEQ ID NOS: 2

<210> SEQ ID NO 1
<211> LENGTH: 1194
<212> TYPE: DNA
<213> ORGANISM: Artificial Sequence
<220> FEATURE:
<223> OTHER INFORMATION: cDNA of AtGRF5

<400> SEQUENCE: 1

```
atgatgagtc taagtggaag tagcgggaga acaataggaa ggcctccatt tacaccaaca        60
caatgggaag aactggaaca tcaagcccta atctacaagt acatggtctc tggtgttcct       120
gtcccacctg agctcatctt ctccattaga agaagcttgg acacttcctt ggtctctaga       180
ctccttcctc accaatccct tggatggggg tgttaccaga tgggatttgg gagaaaacca       240
gatccagagc caggaagatg cagaagaaca gatggtaaga aatggagatg ctcaagagaa       300
gcttacccag attcgaagta ctgtgaaaaa cacatgcaca gaggaagaaa ccgtgccaga       360
aaatctcttg atcagaatca gacaacaaca actcctttaa catcaccatc tctctcattc       420
accaacaaca caacccaag tcccaccttg tcttcttctt cttcctctaa ttcctcttct       480
actacttatt ctgcttcttc ttcttcaatg gatgcctaca gtaacagtaa taggtttggg       540
cttggtggaa gtagtagtaa cactagaggt tatttcaaca gccattctct tgattatcct       600
tatccttcta cttcacccaa acaacaacaa caaactcttc atcatgcttc cgctttgtca       660
cttcatcaaa atactaattc tacttctcag ttcaatgtct tagcctctgc tactgaccac       720
aaagacttca ggtactttca agggattggg gagagagttg gaggagttgg ggagagaacg       780 ttcttttccag aagcatctag aagctttcaa gattctccat accatcatca ccaacaaccg       840
ttagcaacag tgatgaatga tccgtaccac cactgtagta ctgatcataa taagattgat       900
catcatcaca catactcatc ctcatcatca tctcaacatc ttcatcatga tcatgatcat       960
agacagcaac agtgttttgt tttgggcgcc gacatgttca acaaacctac aagaagtgtc      1020
cttgcaaact catcaagaca agatcaaaat caagaagaag atgagaaaga ttcatcagag      1080
tcgtccaaga agtctctaca tcacttcttt ggtgaggact gggcacagaa caagaacagt      1140
tcagattctt ggcttgacct ttcttcccac tcaagactcg acactggtag ctaa            1194
```

<210> SEQ ID NO 2
<211> LENGTH: 397
<212> TYPE: PRT

<213> ORGANISM: Arabidopsis thaliana

<400> SEQUENCE: 2

```
Met Met Ser Leu Ser Gly Ser Ser Gly Arg Thr Ile Gly Arg Pro Pro
1               5                   10                  15
Phe Thr Pro Thr Gln Trp Glu Glu Leu Glu His Gln Ala Leu Ile Tyr
            20                  25                  30
Lys Tyr Met Val Ser Gly Val Pro Val Pro Pro Glu Leu Ile Phe Ser
                35                  40                  45
Ile Arg Arg Ser Leu Asp Thr Ser Leu Val Ser Arg Leu Leu Pro His
50                  55                  60
Gln Ser Leu Gly Trp Gly Cys Tyr Gln Met Gly Phe Gly Arg Lys Pro
65                  70                  75                  80
Asp Pro Glu Pro Gly Arg Cys Arg Arg Thr Asp Gly Lys Lys Trp Arg
                85                  90                  95
Cys Ser Arg Glu Ala Tyr Pro Asp Ser Lys Tyr Cys Glu Lys His Met
            100                 105                 110
His Arg Gly Arg Asn Arg Ala Arg Lys Ser Leu Asp Gln Asn Gln Thr
        115                 120                 125
Thr Thr Thr Pro Leu Thr Ser Pro Ser Leu Ser Phe Thr Asn Asn Asn
130                 135                 140
Asn Pro Ser Pro Thr Leu Ser Ser Ser Ser Ser Asn Ser Ser Ser
145                 150                 155                 160
Thr Thr Tyr Ser Ala Ser Ser Ser Met Asp Ala Tyr Ser Asn Ser
            165                 170                 175
Asn Arg Phe Gly Leu Gly Gly Ser Ser Asn Thr Arg Gly Tyr Phe
        180                 185                 190
Asn Ser His Ser Leu Asp Tyr Pro Tyr Pro Ser Thr Ser Pro Lys Gln
        195                 200                 205
Gln Gln Gln Thr Leu His His Ala Ser Ala Leu Ser Leu His Gln Asn
    210                 215                 220
Thr Asn Ser Thr Ser Gln Phe Asn Val Leu Ala Ser Ala Thr Asp His
225                 230                 235                 240
Lys Asp Phe Arg Tyr Phe Gln Gly Ile Gly Glu Arg Val Gly Val
                245                 250                 255
Gly Glu Arg Thr Phe Phe Pro Glu Ala Ser Arg Ser Phe Gln Asp Ser
            260                 265                 270
Pro Tyr His His His Gln Gln Pro Leu Ala Thr Val Met Asn Asp Pro
        275                 280                 285
Tyr His His Cys Ser Thr Asp His Asn Lys Ile Asp His His His Thr
        290                 295                 300
Tyr Ser Ser Ser Ser Ser Gln His Leu His Asp His Asp His
305                 310                 315                 320
Arg Gln Gln Gln Cys Phe Val Leu Gly Ala Asp Met Phe Asn Lys Pro
                325                 330                 335
Thr Arg Ser Val Leu Ala Asn Ser Ser Arg Gln Asp Gln Asn Gln Glu
            340                 345                 350
Glu Asp Glu Lys Asp Ser Ser Glu Ser Ser Lys Lys Ser Leu His His
        355                 360                 365
Phe Phe Gly Glu Asp Trp Ala Gln Asn Lys Asn Ser Ser Asp Ser Trp
    370                 375                 380
Leu Asp Leu Ser Ser His Ser Arg Leu Asp Thr Gly Ser
385                 390                 395
```

IMPROVING PLANT REGENERATION

CROSS-REFERENCE TO RELATED APPLICATIONS

This application is a U.S. National Phase of International Patent Application No. PCT/EP2020/056743, filed on Mar. 12, 2020, which claims priority to European Application No. 19162189.5, filed Mar. 12, 2019. The entire contents of these applications are incorporated herein by reference in their entirety.

The present invention relates to the field of plant breeding and in particular to the regeneration of plants from cells and other tissues. More particularly, the invention provides methods and means for improving callus and shoot formation and regeneration of plants using hyperphyllin or derivatives thereof.

Plant regeneration involves the in vitro culture of cells, tissues, and organs under defined physical and chemical conditions. Regeneration has long been known to occur in plants. In plants differentiated cells are able to regenerate into the full array of tissues under appropriate culture conditions. Regeneration can involve direct or indirect organogenesis. In direct regeneration, in vitro organs are directly induced from explant tissues; in indirect regeneration, a de novo organ is typically formed from an intermediate tissue, the callus. Plant calli are undifferentiated structures that can give rise to new tissues. Plant leaves, shoots, roots, and embryos can variously be elicited from a growing callus.

Generally, three phases can be recognized throughout plant regeneration. First, somatic cells of explant tissues can respond to hormonal signals to acquire features similar to meristematic cells, a process known as "dedifferentiation". Second, callus cells with organogenic competence are reprogrammed and determined for specific organ formation under the influence of hormone balance. The third regeneration phase, morphogenesis, is independent of exogenously supplied hormones. Thus, exogenous hormone treatment is the critical factor triggering early developmental events in in vitro regeneration.

However, obtaining dedifferentiated cells (callus) that can regenerate into whole plants is not always feasible for many plant species. Sugar beet is known to be recalcitrant for dedifferentiation and plant regeneration. These difficulties were major obstacles for obtaining transgenic sugar beets for example through an *Agrobacterium*-mediated transformation procedure. Since decades breeders and researchers are working on the development of more efficient protocols for transformation and regeneration of plants recalcitrant to callus formation. Typically, such plants show genotypic variations causing drastic differences of rates of callus and shoot formation between different lines (Ivic-Haymes & Smigocki (2005), "Identification of highly regenerative plants within sugar beet (*Beta vulgaris* L.) breeding lines for molecular breeding." *In Vitro Cellular and Developmental Biology-Plant*, 41(4), 483-488; Mishutkina & Gaponenko (2006), "Sugar beet (*Beta vulgaris* L.) morphogenesis in vitro: effects of phytohormone type and concentration in the culture medium, type of explants, and plant genotype on shoot regeneration frequency." *Russian Journal of Genetics*, 42(2), 150-157; Tomita et al. (2013), "Evaluation of the potential for somatic embryogenesis in sugar beet (*Beta vulgaris* L.) breeding lines and improvement of regeneration efficiency." *Plant Biotechnology*, 30(5), 479-487.). Often regeneration for certain genotypes is not feasible at all. Kishchenko et al. 2005 ("Production of transgenetic sugar-beet (*Beta vulgaris* L.) plants resistant to phosphinothricin." *Cell biology international*, 29(1), 15-19.) and Kagami at el. 2015 ("Sugar beet (*Beta vulgaris* L.)." *Agrobacterium Protocols: Volume* 1, 335-347.) disclose well-known protocols for the transformation of sugar beet, however these protocols show strong genotype dependency.

Chaudhury et al. (1993. "amp1—a mutant with high cytokinin levels and altered embryonic pattern, faster vegetative growth, constitutive photomorphogenesis and precocious flowering." *The Plant Journal*, 4(6), 907-916.) describes first an amp1 (ALTERED MERISTEM PROGRAM1) mutant of *Arabidopsis thaliana*, which has a phenotype altered in three different aspects of plant development; spatial pattern, photomorphogenetic growth, and initiation of flowering. Amp1 (At3G54720) belongs to the $Zn^{2+}$-dependent metalloproteases of the M28B peptidase family (Helliwell et al., 2001. "The *Arabidopsis* AMP1 gene encodes a putative glutamate carboxypeptidase." *The Plant Cell*, 13(9), 2115-2125.). AMP1 antagonistically regulates embryo and meristem development in *Arabidopsis* and is involved in shoot apical meristem development. The amp1 mutant displays enlarged shoot apical meristem (Vidaurre et al., 2007. "AMP1 and MP antagonistically regulate embryo and meristem development in *Arabidopsis*." *Development*, 134(14), 2561-2567.). Mordhorst et al. (1998. "Somatic embryogenesis in *Arabidopsis thaliana* is facilitated by mutations in genes repressing meristematic cell divisions." *Genetics*, 149(2), 549-563.) shows that amp1 mutant facilitates somatic embryogenesis in *Arabidopsis thaliana*. In 2016 the authors of Poretska et al. ("The small molecule hyperphyllin enhances leaf formation rate and mimics shoot meristem integrity defects associated with AMP1 deficiency." *Plant physiology*, pp-01633.) demonstrated that the small molecule hyperphyllin (HP) and three derivatives thereof (A1, A2 and A3) enhance leaf formation rate and mimic amp1 mutant phenotype. HP treatment of *Arabidopsis thaliana* leads to changes in stress response and biotic interaction related gene expression. Even though there seems to be an interaction between AMP1 and HP treatment, the functional relation is not yet fully understood.

Surprisingly, the inventors found that by applying the chemical HP or a derivative thereof to leaf tissue explants of sugar beet, the induction of callus even from recalcitrant genotypes was significantly promoted. The resulting callus could be regenerated into normal shoots and the produced plants show a normal phenotype. Induced callus was robust enough to be amenable for transformation and gene editing. The prior art describes the effect of the chemical HP in mimicking amp1 mutant in *Arabidopsis* only with enlarged shoot apical meristem. Although amp1 mutant displays enhanced regeneration capability, such favorable boosting effect in callus formation induced by the chemical HP has never been shown neither in *Arabidopsis* nor any other crops.

Thus, a first aspect of the present invention is the use of hyperphyllin or a derivative thereof, in a method for inducing plant callus formation.

The present invention provides a method for inducing callus formation from plant cells, comprising incubating the plant cells in the presence of hyperphyllin or a derivative thereof (FIG. 1).

Hyperphyllin is N-[4-Amino-2-chlorophenyl]-2,4-dichlorobenzamide reproduced below.

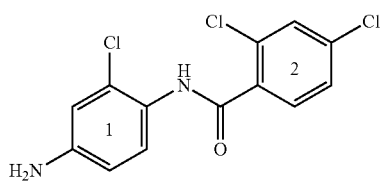 [SMILES: Nc1ccc(NC(=O)c2ccc(Cl)cc2Cl)c(Cl)c1]

In addition to hyperphyllin, derivatives thereof may also be used in the method of the invention. Preferred derivatives are based on benzanilide substituted at one or more positions of one or both phenyl rings 1 and 2, in particular at ortho and/or para position(s) with respect to the amide functionality. Substituents can be selected inter alia from halogens, e.g. Cl or F, amino groups, e.g —$NH_2$, substituted amino groups —$NHR$ and —$NR_2$ wherein R may for example be C1-4 alkyl such as methyl or ethyl and alkyl groups, e.g. C1-4 alkyl such as methyl or ethyl and alkyl groups. Most preferably, the derivatives are selected from compounds of formulae A1, A2 and A3 reproduced below.

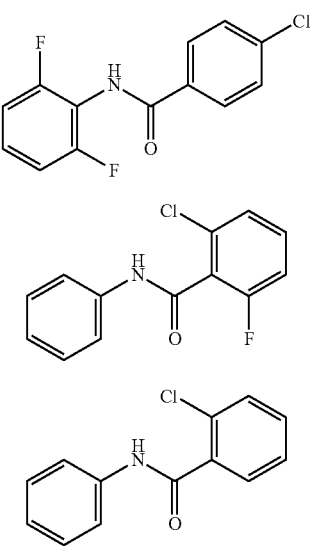

The presence of hyperphyllin or a derivative thereof in the incubation step can be achieved, for example, by incubating the plant cells in a medium containing hyperphyllin or a derivative thereof, or by introducing hyperphyllin or a derivative thereof directly into the plant cells, for example via bombardment, electroporation or microinjection. Preferably, callus formation is induced in a culture medium containing hyperphyllin or derivatives thereof.

In principle, it is sufficient to use only one plant cell for inducing callus formation. Thus, if the plural "plant cells" is used in the following the wording must not be understood in that a minimum number of plant cells would be required.

Plant cells suitable for inducing callus tissue include embryonic plant cells and somatic plant cells. The way how these plant cells are provided is not important for the method according to the present invention. Plant cells can be used either in isolated form or as part of a plant tissue. For example, embryonic or somatic plant cells can be provided from an explant isolated from a plant. Either the cells are isolated from the explant or the explant is directly used for the induction of callus tissue. Which part of a plant is eligible for obtaining an explant depends on the particular plant species. Generally, suitable plant cells can be obtained from hypocotyl, shoot, leaves, buds, flowers, petiols and roots of a plant.

Surprisingly, it was found that hyperphyllin and derivatives thereof are suitable for inducing callus formation even in recalcitrant plant species or plant genotypes.

The incubating step can be carried out using any culture medium known in the art, in particular a medium commonly used for inducing callus formation. Depending on the plant in question, the composition of the medium may vary. In principle, several types of basal salt mixtures can be added to the medium, but preferably, the medium comprises modified Murashige and Skoog (MS) medium, White's medium, or woody plant medium, most preferably MS medium. Previous studies indicate that callus induction is facilitated in the presence of appropriate amounts and concentrations of auxins and cytokinins alone or in combination with each other in MS medium. According to the invention, these components can also be added preferentially to the culture medium. Exemplary auxins include naphthalene acetic acid (NAA), indole-3-acetic acid (IAA) and indole-3-butyric acid (IBA). Exemplary cytokinins include 6-Benzylaminopurine (BAP) and 6-furfurylamino-purine (kinetin).

The concentration of hyperphyllin or a derivative thereof in the medium can range from about 5 µM up to about 200 µM, preferably from about 10 µM up to about 100 µM, more preferably from about 20 µM up to about 80 µM, most preferably from about 30 µM up to about 50 µM. In order to achieve the desired boost of callus formation, the concentration of hyperphyllin or a derivative thereof in the medium is preferably in a range from about 20 µM to about 80 µM, more preferably from about 30 µM to about 50 µM. In addition, further additives for the induction of callus tissue can be added which are well known in the art. For example, a culture medium for use in the induction of callus formation according to the invention may comprise MS salts, sucrose, BAP and hyperphyllin. According to another aspect of the invention it was found, that callus tissue obtained according to the above described method in the presence of hyperphyllin or a derivative thereof is surprisingly well suited to generate shoots and finally whole plants even for recalcitrant plant species or plant genotypes. Thus, using the approach of the invention it is possible to improve indirect regeneration in recalcitrant plant species or plant genotypes.

Accordingly, the invention provides a method for producing plant shoots, comprising
(i) inducing callus formation according to the method described above to yield callus tissue, and
(ii) cultivating the callus tissue under conditions suitable to induce shoot formation.

The cultivating step can be carried out using any medium well-known in the art for growing callus tissue and inducing shoot formation. Depending on the plant in question, these conditions may vary. In principle, several types of basal salt mixtures can be used for culturing callus tissue, but most preferred, the medium comprises modified Murashige and Skoog medium, White's medium, or woody plant medium. In order to facilitate shoot induction, one or more additives can be used in the culture medium. The culture medium can be supplemented with plant growth regulators, such as auxins, and cytokinins. Vitamins can be provided to enhance growth, such as Gamborg B5 vitamins. Enrichment with nitrogen, phosphorus and potassium also proved to be helpful. For example, a culture medium for use in the cultivation of callus tissue to yield shoot formation may comprise MS salts, sucrose, BAP and kanamycin.

According to another aspect of the invention, the beneficial effect of hyperphyllin or derivatives thereof, in particular derivatives of formulae A1, A2 or A3, on callus formation can be exploited in methods of producing transgenic plants as well as in methods for producing genetically modified plants. It was found, that in recalcitrant plant species or plant genotypes, transformation efficiency can be improved by using hyperphyllin or derivatives thereof, in particular derivatives of formulae A1, A2 or A3. The regeneration of plants from modified plant cells that have been transformed or gene edited and possibly have a modified genome is significantly improved when hyperphyllin or derivatives thereof, in particular derivatives of formulae A1, A2 or A3 are present in the step of callus formation.

Accordingly, the invention provides a method for producing a transgenic plant, comprising the following steps:
  (a) Inducing callus formation according to the method described above to yield callus tissue,
  (b) Introducing into a plant cell to be used in step (a) and/or into a cell of the callus tissue obtained in step (a) at least one nucleotide sequence of interest or at least one polypeptide of interest,
  (c) Cultivating the callus tissue obtained from steps (a) and (b) according to the method described above to yield plant shoots, and
  (d) Regenerating a transgenic plant.

Step (a) of inducing callus formation includes incubating plant cells in the presence of hyperphyllin or derivatives thereof, in particular derivatives of formulae A1, A2 or A3. Suitable plant cells and conditions are as defined above.

In step (b), a cell is transformed by introducing a nucleic acid molecule into the cell in a manner to cause stable or transient presence of the nucleic acid sequence, preferably stable or transient expression of the nucleic acid sequence or by introducing a polypeptide into the cell in a manner to cause transient presence. Stable presence of for example a DNA sequence means that said DNA sequence is stable incorporated into the genome of the cell. Stable expression refers to the expression of for example a DNA sequence that is stable incorporated into the genome of the cell. Transformation of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium*-mediated transformation.

According to one embodiment of the present invention, the at least one nucleotide sequence of interest or at least one polypeptide of interest is introduced into the plant cell to be used in step (a) of inducing callus formation. It is understood that in this case step (b) is carried out before step (a). According to another embodiment of the invention the at least one nucleotide sequence of interest or at least one polypeptide of interest is introduced into a cell of the callus obtained in step (a). It is understood that in this case, step (b) is carried out after step (a). Additionally, it is possible to introduce nucleotide sequences of interest or polypeptides of interest both into the cell to be used for callus formation and into the cell of the callus resulting from step (a). According to this embodiment the method includes the following steps:

(i) introducing into a plant cell at least one nucleotide sequence of interest or at least one polypeptide of interest,
  (ii) inducing callus formation from the cell obtained in step (i) and
  (iii) introducing at least one nucleotide sequence of interest or at least one polypeptide of interest into a cell of the callus obtained in step (ii).

The step of introducing the at least one nucleotide sequence of interest or at least one polypeptide of interest can be performed using any suitable method commonly known in the art. A number of methods as also mentioned above is available to transfer nucleic acids of interest or polypeptides into plant cells. An exemplary vector mediated method for introducing DNA molecules is *Agrobacterium*-mediated transformation, as described, for example, by Lindsey & Gallois, 1990, Journal of Experimental Botany, and Kischenko et al., 2005, Cell Biology International for sugar beet, by Ishida et al., 2007, ("*Agrobacterium*-mediated transformation of maize." *Nature protocols,* 2(7), 1614-1621) for corn, or by the PureWheat Technology from Japan Tobacco company for wheat. Other suitable techniques also suitable for introducing RNA molecules or polypeptides include particle bombardment and electroporation.

The nucleotide sequence of interest according to the invention may be a DNA or RNA sequence, e.g. mRNA, siRNA, miRNA, tRNA etc. More particularly, the nucleotide sequence of interest may encode a polypeptide conferring at least one phenotypic trait. Preferably, the phenotypic trait conferred by the polypeptide can be selected from the group consisting of resistance/tolerance to biotic stress, including pathogen resistance/tolerance, wherein the pathogen can be a virus, bacterial, fungal or animal pathogen, resistance/tolerance to abiotic stress including chilling resistance/tolerance, drought stress resistance/tolerance, osmotic resistance/tolerance, heat stress resistance/tolerance, cold or frost stress resistance/tolerance, oxidative stress resistance/tolerance, heavy metal stress resistance/tolerance, salt stress or water logging resistance/tolerance, lodging resistance/tolerance, shattering resistance/tolerance, or resistance/tolerance against one or more herbicides like glyphosate, glufosinate, 2,4-D, Dicamba, ALS inhibitors et cetera. The at least one phenotypic trait of interest can also be selected from the group consisting of the modification of a further agronomic trait of interest including yield increase, flowering time modification, seed color modification, endosperm composition modification, nutritional content modification or metabolic engineering of a pathway of interest. Furthermore, the nucleotide sequence of interest may encode or may be a component of a gene editing machinery, e.g. a gRNA, a crRNA, a tracrRNA, a sgRNA, a nuclease, a disarmed nuclease, a nickase, a disarmed nickase, a base editor, a TALE recognition domain or a zinc finger recognition domain or a fusion protein comprising such recognition domain, etc.

A nucleic acid (molecule) or nucleotide (sequence) or polynucleotide, as used herein, refers to both DNA and RNA. DNA also includes cDNA and genomic DNA. A nucleic acid molecule can be single- or double-stranded, and can be synthesized chemically or produced by biological expression in vitro or even in vivo.

It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

The polypeptide of interest according to the invention may be a transcription factor, a protein component of a gene editing machinery, like a nuclease, a nickase, a base editor, a recognition domain of a TAL effector or a zinc finger effector, or may be a polypeptide conferring phenotypic trait which can be selected from the group consisting of resistance/tolerance against one or more herbicides like glyphosate, glufosinate, 2,4-D, Dicamba, ALS inhibitors, color marker, fluorescence marker, resistance/tolerance to biotic stress, including pathogen resistance/tolerance, wherein the pathogen can be a virus, bacterial, fungal or animal pathogen, resistance/tolerance to abiotic stress including chilling resistance/tolerance, drought stress resistance/tolerance, osmotic resistance/tolerance, heat stress resistance/tolerance, cold or frost stress resistance/tolerance, oxidative stress resistance/tolerance, heavy metal stress resistance/tolerance, salt stress or water logging resistance/tolerance, lodging resistance/tolerance, shattering resistance/tolerance, or et cetera. A polypeptide of interest can be synthesized chemically or produced by biological expression in vitro or even in vivo.

In steps (c) and (d) of the above method for producing a transgenic plant, the modified callus tissue including plant cells that have been transformed are regenerated into a whole (fertile) plant. Therefore, in step (c) the callus tissue is cultivated under conditions suitable to induce shoot formation and finally regenerated into a whole plant in step (d).

Regeneration techniques rely on manipulation of certain phytohormones in a tissue culture growth medium, occasionally relying on a biocide and/or herbicide marker that can been introduced together with the desired nucleotide sequence(s) of interest. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, protoplasts, immature or mature embryos, embryonic tissue, meristematic tissues, organs, or parts thereof. Such regeneration techniques are described generally in Klee (1987) Ann. Rev. of Plant Phys. 38:467486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

Further, the invention also provides a method for producing a genetically modified plant, comprising the following steps (a) Inducing callus formation from at least one plant cell according to the method described above to yield callus tissue, (b) Modifying the genome of a plant cell to be used in step (a) and/or of a cell of the callus tissue obtained in step (a) by introducing into said cell a single stranded DNA break (SSB) inducing enzyme or a double stranded DNA break (DSB) inducing enzyme which preferably recognizes a predetermined site in the genome of said cell and optionally a repair nucleic acid molecule, and/or a base editor fused to a catalytically impaired SSB or DSB inducing enzyme or fused to a SSB inducing enzyme which preferably recognizes a predetermined site in the genome of said cell, wherein the modification of said genome is selected from
i. a replacement of at least one nucleotide;
ii. a deletion of at least one nucleotide;
iii. an insertion of at least one nucleotide; or
iv. any combination of i.-iii, (c) Cultivating the callus tissue obtained from steps (a) and (b) according to the method described above to yield plant shoots, and (d) Regenerating a genetically modified plant.

Step (a) of inducing callus formation is performed by the method described herein above. Accordingly, callus formation is induced in the presence of hyperphyllin or derivatives thereof; which can be added to the medium or directly into the plant cells.

In step (b), modifying the genome of the cell may be accomplished by means of a single stranded DNA break inducing (SSB) enzyme or a double-stranded DNA break (DSB) inducing enzyme which preferably recognizes a predetermined site in the genome of said cell, and/or by means of a base editor fused to a catalytically impaired SSB or DSB inducing enzyme or fused to a SSB inducing enzyme which preferably recognizes a predetermined site in the genome of said cell.

The step of modifying the genome can be carried out before and/or after induction of callus formation. Thus, according to a first aspect of the invention, the genome of a plant cell is modified as described in step (b) and the resulting modified plant cell is then used in a subsequent step (a) of inducing callus formation. According to another aspect of the invention, step (a) of inducing callus formation is carried out first and subsequently at least one cell of the resulting callus tissue is modified in step (b) by means of a single stranded DNA break (SSB) inducing enzyme or a double-stranded DNA break-inducing enzyme and/or by means of a base editor fused to a catalytically impaired SSB or DSB inducing enzyme or fused to a SSB inducing enzyme. Furthermore, it is possible to modify the genome of both the plant cell to be used in the step of callus formation and a cell of the callus tissue resulting from the step of inducing callus formation. According to this aspect of the invention, the method includes the steps of (i) modifying the genome of a plant cell,
(ii) inducing callus formation from the cell resulting from step (i) and
(iii) modifying the genome of a cell of the callus tissue obtained in step (ii).

As used herein, a "double-stranded DNA break inducing enzyme" or "DSB inducing enzyme" or "DSBI enzyme" is an enzyme capable of inducing a double-stranded DNA break at a particular nucleotide sequence, called the "recognition site" or "predetermined site" or "predetermined target site". Accordingly, a "single-stranded DNA break inducing enzyme", "enzyme inducing a single-stranded break", or "SSBI enzyme" is an enzyme capable of inducing a single-stranded DNA or RNA break at a particular nucleotide sequence, called the "recognition site" or "predetermined (target) site" or "predefined (target) site".

In recent years, many suitable nucleases, especially tailored endonucleases have been developed comprising The double-stranded DNA break (DSB)-inducing enzyme can, for example, be selected from the group consisting of meganuclease, TAL effector nuclease, zinc finger nuclease, CRISPR nucleases, comprising, for example, Cas9, Cpf1, Csm1, CasX or CasY nucleases as part of the Clustered Regularly Interspaced Short Palindromic Repeats (CRISPR) system. Thus, in a preferred aspect of the invention, the genome modification are mediated by a DSB- or SSB-inducing enzyme or a variant thereof selected from a CRISPR/Cas endonuclease, preferably a CRISPR/Cas9 endonuclease a CRISPR/Cpf1 endonuclease, a CRISPR/ MAD7 endonuclease or a CRISPR/Csm1 endonuclease, a zinc finger nuclease (ZFN), a homing endonuclease, a meganuclease and a TAL effector nuclease.

Rare-cleaving endonucleases are DSBI enzymes that have a recognition site of preferably about 14 to 70 consecutive nucleotides, and therefore have a very low frequency of cleaving, even in larger genomes such as most plant genomes. Homing endonucleases, also called meganucleases, constitute a family of such rare-cleaving endonucleases. They may be encoded by introns, independent genes or intervening sequences, and present striking structural and functional properties that distinguish them from the more classical restriction enzymes, usually from bacterial restriction-modification Type II systems. Their recognition sites have a general asymmetry which contrast to the characteristic dyad symmetry of most restriction enzyme recognition sites. Several homing endonucleases encoded by introns or inteins have been shown to promote the homing of their respective genetic elements into allelic intronless or inteinless sites. By making a site-specific double strand break in the intronless or inteinless alleles, these nucleases create recombinogenic ends, which engage in a gene conversion process that duplicates the coding sequence and leads to the insertion of an intron or an intervening sequence at the DNA level. A list of other rare cleaving meganucleases and their respective recognition sites is provided in Table I of WO 03/004659 (pages 17 to 20) (incorporated herein by reference).

Furthermore, methods are available to design custom-tailored rare-cleaving endonucleases that recognize basically any target nucleotide sequence of choice. Briefly, chimeric restriction enzymes can be prepared using hybrids between a zinc-finger domain designed to recognize a specific nucleotide sequence and the non-specific DNA-cleavage domain from a natural restriction enzyme, such as FokI. Such methods have been described e.g. in WO 03/080809, WO 94/18313 or WO 95/09233 and in Isalan et al., 2001, Nature Biotechnology 19, 656-660; Liu et al. 1997, Proc. Natl. Acad. Sci. USA 94, 5525-5530).

Another example of custom-designed endonucleases includes the so-called TALE nucleases (TALENs), which are based on transcription activator-like effectors (TALEs) from the bacterial genus *Xanthomonas* fused to the catalytic domain of a nuclease (e.g. FokI or a variant thereof). The DNA binding specificity of these TALEs is defined by repeat-variable diresidues (RVDs) of tandem-arranged 34/35-amino acid repeat units, such that one RVD specifically recognizes one nucleotide in the target DNA. The repeat units can be assembled to recognize basically any target sequences and fused to a catalytic domain of a nuclease create sequence specific endonucleases (see e.g. Boch et al., 2009, Science 326:p1509-1512; Moscou and Bogdanove, 2009, Science 326:p1501; and WO 2010/079430, WO 2011/072246, WO 2011/154393, WO 2011/146121, WO 2012/001527, WO 2012/093833, WO 2012/104729, WO 2012/138927, WO 2012/138939). WO2012/138927 further describes monomeric (compact) TALENs and TALENs with various catalytic domains and combinations thereof.

Recently, a new type of customizable endonuclease system has been described; the so-called CRISPR/Cas system. A CRISPR system in its natural environment describes a molecular complex comprising at least one small and individual non-coding RNA in combination with a Cas nuclease or another CRISPR nuclease like a Cpf1 nuclease (Zetsche et al., "Cpf1 Is a Single RNA-Guides Endonuclease of a Class 2 CRISPR-Cas System", Cell, 163, pp. 1-13, October 2015), a MAD7 nuclease or a Csm1 nuclease which can produce a specific DNA double-stranded break. Presently, CRISPR systems are categorized into 2 classes comprising five types of CRISPR systems, the type II system, for instance, using Cas9 as effector and the type V system using Cpf1 as effector molecule (Makarova et al., Nature Rev. Microbiol., 2015). In artificial CRISPR systems, a synthetic non-coding RNA and a CRISPR nuclease and/or optionally a modified CRISPR nuclease, modified to act as nickase or lacking any nuclease function, can be used in combination with at least one synthetic or artificial guide RNA or gRNA combining the function of a crRNA and/or a tracrRNA (Makarova et al., 2015, supra). The immune response mediated by CRISPR/Cas in natural systems requires CRISPR-RNA (crRNA), wherein the maturation of this guiding RNA, which controls the specific activation of the CRISPR nuclease, varies significantly between the various CRISPR systems which have been characterized so far. Firstly, the invading DNA, also known as a spacer, is integrated between two adjacent repeat regions at the proximal end of the CRISPR locus. Type II CRISPR systems code for a Cas9 nuclease as key enzyme for the interference step, which system contains both a crRNA and also a trans-activating RNA (tracrRNA) as the guide motif. These hybridize and form double-stranded (ds) RNA regions which are recognized by RNAseIII and can be cleaved in order to form mature crRNAs. These then in turn associate with the Cas molecule in order to direct the nuclease specifically to the target nucleic acid region. Recombinant gRNA molecules can comprise both the variable DNA recognition region and also the Cas interaction region and thus can be specifically designed, independently of the specific target nucleic acid and the desired Cas nuclease.

As a further safety mechanism, PAMs (protospacer adjacent motifs) must be present in the target nucleic acid region; these are DNA sequences which follow on directly from the Cas9/RNA complex-recognized DNA. The PAM sequence for the Cas9 from *Streptococcus pyogenes* has been described to be "NGG" or "NAG" (Standard IUPAC nucleotide code) (Jinek et al, "A programmable dual-RNA-guided DNA endonuclease in adaptive bacterial immunity", Science 2012, 337: 816-821). The PAM sequence for Cas9 from *Staphylococcus aureus* is "NNGRRT" or "NNGRR(N)". Further variant CRISPR/Cas9 systems are known. Thus, a *Neisseria meningitidis* Cas9 cleaves at the PAM sequence NNNNGATT. A *Streptococcus thermophilus* Cas9 cleaves at the PAM sequence NNAGAAW. Recently, a further PAM motif NNNNRYAC has been described for a CRISPR system of *Campylobacter* (WO 2016/021973 A1). For Cpf1 nucleases it has been described that the Cpf1-crRNA complex, without a tracrRNA, efficiently recognize and cleave target DNA proceeded by a short T-rich PAM in contrast to the commonly G-rich PAMs recognized by Cas9 systems (Zetsche et al., supra). Furthermore, by using modified CRISPR polypeptides, specific single-stranded breaks can be obtained. The combined use of Cas nickases with various recombinant gRNAs can also induce highly specific DNA double-stranded breaks by means of double DNA nicking. By using two gRNAs, moreover, the specificity of the DNA binding and thus the DNA cleavage can be optimized. Further CRISPR effectors like CasX and CasY effectors originally described for bacteria, are meanwhile available and represent further effectors, which can be used for genome engineering purposes (Burstein et al., "New CRISPR-Cas systems from uncultivated microbes", Nature, 2017, 542, 237-241).

The cleavage site of a DSBI/SSBI enzyme relates to the exact location on the DNA or RNA where the break is induced. The cleavage site may or may not be comprised in (overlap with) the recognition site of the DSBI/SSBI enzyme and hence it is said that the cleavage site of a DSBI/SSBI enzyme is located at or near its recognition site. The recognition site of a DSBI/SSBI enzyme, also sometimes referred to as binding site, is the nucleotide sequence that is (specifically) recognized by the DSBI/SSBI enzyme and determines its binding specificity. For example, a TALEN or ZNF monomer has a recognition site that is determined by their RVD repeats or ZF repeats respectively, whereas its cleavage site is determined by its nuclease domain (e.g. FokI) and is usually located outside the recognition site. In case of dimeric TALENs or ZFNs, the cleavage site is located between the two recognition/binding sites of the respective monomers, this intervening DNA or RNA region where cleavage occurs being referred to as the spacer region.

A person skilled in the art would be able to either choose a DSBI/SSBI enzyme recognizing a certain recognition site and inducing a DSB or SSB at a cleavage site at or in the vicinity of the preselected/predetermined site or engineer such a DSBI/SSBI enzyme. Alternatively, a DSBI/SSBI enzyme recognition site may be introduced into the target genome using any conventional transformation method or by crossing with an organism having a DSBI/SSBI enzyme recognition site in its genome, and any desired nucleic acid may afterwards be introduced at or in the vicinity of the cleavage site of that DSBI/SSBI enzyme.

In some embodiments, the induction of one or more double-stranded breaks or one or more single strand breaks is followed by non-homologous end joining (NHEJ) and/or by homology directed repair of the break(s) though a homologous recombination mechanism (HDR). NHEJ and HDR are two major and distinct pathways to repair breaks. Homologous recombination requires the presence of a homologous sequence as a template (e.g., repair nucleic acid molecule or "donor") to guide the cellular repair process and the results of the repair are error-free and predictable. In the absence of a template (or repair nucleic acid molecule or "donor") sequence for homologous recombination, the cell typically attempts to repair the break via the process of non-homologous end-joining (NHEJ).

In a particularly preferred aspect of this embodiment, a repair nucleic acid molecule is additionally introduced into the plant cell.

As used herein, a "repair nucleic acid molecule" is a single-stranded or double-stranded DNA molecule or RNA molecule that is used as a template for modification of the genomic DNA at the preselected site in the vicinity of or at the cleavage site. As used herein, "use as a template for modification of the genomic DNA", means that the repair nucleic acid molecule is copied or integrated at the preselected site by homologous recombination between the flanking region(s) and the corresponding homology region(s) in the target genome flanking the preselected site, optionally in combination with non-homologous end-joining (NHEJ) at one of the two end of the repair nucleic acid molecule (e.g. in case there is only one flanking region). Integration by homologous recombination will allow precise joining of the repair nucleic acid molecule to the target genome up to the nucleotide level, while NHEJ may result in small insertions/deletions at the junction between the repair nucleic acid molecule and genomic DNA.

In various embodiments of the aspects described herein, a modification of the genome occurs in which the genome has changed by at least one nucleotide. Modification of the genome can occur by insertion of a transgene, preferably an expression cassette comprising a transgene of interest, replacement of at least one nucleotide and/or a deletion of at least one nucleotide and/or an insertion of at least one nucleotide, as long as it results in a total change of at least one nucleotide compared to the nucleotide sequence of the preselected genomic target site before modification, thereby allowing the identification of the modification, e.g., by techniques such as sequencing or PCR analysis and the like, of which the skilled person will be well aware.

A "base editor" as used herein refers to a protein or a fragment thereof having the capacity to mediate a targeted base modification, i.e., the conversion of a base of interest resulting in a point mutation of interest. Preferably, the at least one base editor in the context of the present invention is temporarily or permanently fused to at least one DSBI enzyme, or optionally to a component of at least one DSBI. The fusion can be covalent and/or non-covalent. Multiple publications have shown targeted base conversion, primarily cytidine (C) to thymine (T), using a CRISPR/Cas9 nickase or non-functional nuclease linked to a cytidine deaminase domain, Apolipoprotein B mRNA-editing catalytic polypeptide (APOBEC1), e.g., APOBEC derived from rat. The deamination of cytosine (C) is catalysed by cytidine deaminases and results in uracil (U), which has the base-pairing properties of thymine (T). Most known cytidine deaminases operate on RNA, and the few examples that are known to accept DNA require single-stranded (ss) DNA. Studies on the dCas9-target DNA complex reveal that at least nine nucleotides (nt) of the displaced DNA strand are unpaired upon formation of the Cas9-guide RNA-DNA 'R-loop' complex (Jore et al., Nat. Struct. Mol. Biol., 18, 529-536 (2011)). Indeed, in the structure of the Cas9 R-loop complex, the first 11 nt of the protospacer on the displaced DNA strand are disordered, suggesting that their movement is not highly restricted. It has also been speculated that Cas9 nickase-induced mutations at cytosines in the non-template strand might arise from their accessibility by cellular cytosine deaminase enzymes. It was reasoned that a subset of this stretch of ssDNA in the R-loop might serve as an efficient substrate for a dCas9-tethered cytidine deaminase to effect direct, programmable conversion of C to U in DNA (Komor et al., supra). Recently, Goudelli et al ((2017). Programmable base editing of A•T to G•C in genomic DNA without DNA cleavage. Nature, 551(7681), 464.) described adenine base editors (ABEs) that mediate the conversion of A•T to G•C in genomic DNA.

As used herein, "a modification of the genome", means that the genome has changed by at least one nucleotide. This can occur by replacement of at least one nucleotide and/or a deletion of at least one nucleotide and/or an insertion of at least one nucleotide, as long as it results in a total change of at least one nucleotide compared to the nucleotide sequence of the preselected genomic target site before modification, thereby allowing the identification of the modification, e.g. by techniques such as sequencing or PCR analysis and the like, of which the skilled person will be well aware.

As used herein "recognition site" or "a preselected (target) site" or "predefined (target) site" indicates a particular nucleotide sequence in the genome (e.g. the nuclear genome) at which location it is desired to insert, replace and/or delete one or more nucleotides. This can e.g. be an endogenous locus or a particular nucleotide sequence in or linked to a previously introduced foreign DNA or transgene. The preselected site can be a particular nucleotide position at (after) which it is intended to make an insertion of one or more nucleotides. The preselected site can also comprise a sequence of one or more nucleotides which are to be exchanged (replaced) or deleted.

As used in the context of the present application, the term "about" means+/−10% of the recited value, preferably +/−5% of the recited value. For example, about 100 nucleotides (nt) shall be understood as a value between 90 and 110 nt, preferably between 95 and 105.

As used herein, a "flanking region", is a region of the repair nucleic acid molecule having a nucleotide sequence which is homologous to the nucleotide sequence of the DNA region flanking (i.e. upstream or downstream) of the preselected site. It will be clear that the length and percentage sequence identity of the flanking regions should be chosen such as to enable homologous recombination between said flanking regions and their corresponding DNA region upstream or downstream of the preselected site. The DNA region or regions flanking the preselected site having homology to the flanking DNA region or regions of the repair nucleic acid molecule are also referred to as the homology region or regions in the genomic DNA.

To have sufficient homology for recombination, the flanking DNA regions of the repair nucleic acid molecule may vary in length, and should be at least about 10 nt, about 15 nt or about 20 nt in length. However, the flanking region may be as long as is practically possible (e.g. up to about 100-150 kb such as complete bacterial artificial chromosomes (BACs). Preferably, the flanking region will be about 50 nt to about 2000 nt, e.g. about 100 nt, 200 nt, 500 nt or 1000 nt. Moreover, the regions flanking the DNA of interest need not be identical to the homology regions (the DNA regions flanking the preselected site) and may have between about 80% to about 100% sequence identity, preferably about 95% to about 100% sequence identity with the DNA regions flanking the preselected site. The longer the flanking region, the less stringent the requirement for homology. Furthermore, to achieve exchange of the target DNA sequence at the preselected site without changing the DNA sequence of the adjacent DNA sequences, the flanking DNA sequences should preferably be identical to the upstream and downstream DNA regions flanking the preselected site.

As used herein, "upstream" indicates a location on a nucleic acid molecule which is nearer to the 5' end of said nucleic acid molecule. Likewise, the term "downstream" refers to a location on a nucleic acid molecule which is nearer to the 3' end of said nucleic acid molecule. For avoidance of doubt, nucleic acid molecules and their sequences are typically represented in their 5' to 3' direction (left to right).

In order to target sequence modification at the preselected site, the flanking regions must be chosen so that 3' end of the upstream flanking region and/or the 5' end of the downstream flanking region align(s) with the ends of the predefined site. As such, the 3' end of the upstream flanking region determines the 5' end of the predefined site, while the 5' end of the downstream flanking region determines the 3' end of the predefined site.

As used herein, said preselected site being located outside or away from said cleavage (and/or recognition) site, means that the site at which it is intended to make the genomic modification (the preselected site) does not comprise the cleavage site and/or recognition site of the SSBI or DSBI enzyme, i.e. the preselected site does not overlap with the cleavage (and/or recognition) site. Outside/away from in this respect thus means upstream or downstream of the cleavage (and/or recognition) site.

Steps (c) and (d) of the above method for producing a genetically modified plant are carried out as described above in the context of producing a transgenic plant. Thus, the modified plant cell that has been gene edited and possibly has a modified genome is regenerated into a whole (fertile) plant.

Still a further aspect of the present invention relates to the production of haploid and double haploid plant embryos and plants. It was found that the beneficial effect of hyperphillin and derivatives thereof on callus formation can also be exploited for producing haploid and double haploid plant embryos. Thus, the present invention provides a method for producing a haploid plant embryo, comprising the steps
  (a) Inducing callus formation from an immature male gametophyte or a microspore according to the method described above to yield callus tissue,
  (b) Cultivating the callus tissue obtained in step (a) according to the method described above to yield plant shoots, and
  (c) Optionally conducting chromosome doubling.

The haploid or double haploid plant embryo obtained in this manner can then be regenerated into a mature plant. Thus, the present invention also provides a method for producing a haploid or double haploid plant, comprising the steps
  (a) Inducing callus formation from an immature male gametophyte or a microspore according to the method described above to yield callus tissue,
  (b) Cultivating the callus tissue obtained in step (a) according to the method described above to yield plant shoots,
  (c) Optionally conducting chromosome doubling, and
  (d) Regenerating a haploid or double haploid plant.

Haploids are plants (sporophytes) that contain a gametic chromosome number. Spontaneous haploid individuals have been identified in several plant species. However, spontaneous evidence is a rare event, resulting in a limited application. Hence artificial haploid induction is necessary for potential use in breeding. Induction protocols substantially vary, not only among species but also among genotypes of the same species.

In the methods of the present invention, immature male gametophytes or microspores are used as the starting material for producing haploids and double haploids. In step (a), callus formation is induced under conditions promoting the growing of callus tissue as described above. The method relies on the ability of immature male gametophytes and microspores to convert their developmental pathway from gametophytic (leading to mature pollen grain) to sporophytic, resulting in cell division at a haploid level followed by formation of calluses and embryos. This process can be induced by several factors. The most widely used triggering factors are temperature pre-treatment, sucrose and nitrogen starvation and osmotic stress. In addition to stress treatments, the culture media constituents have a significant effect. Depending on the plant concerned, a skilled person can choose among a variety of well-known methods suitable to induce callus formation from immature male gametophytes or microspores.

In step (b), the callus tissue is cultivated under conditions described in detail herein above, to induce shoot formation.

Due to the absence of one set of homologous chromosomes in haploid plants, meiosis cannot occur, so there is no seed set. Therefore, duplication of the chromosome complement can be accomplished in step (c) of the above methods for producing haploid and double haploid plant embryos and plants. Various techniques have been applied over several decades and are well known to the skilled person. The most frequently used application is treatment with anti-microtubule drugs, such as colchicine (originally extracted from autumn crocus *Colchicum autumnale*), which inhibits microtubule polymerization by binding to tubulin. Although colchicine is highly toxic, used at a millimolar concentration and known to be more efficient in animal than in plant tissues, it is still the most widely used doubling agent. Other options are oryzalin, amiprophosmethyl (APM), trifluralin and pronamide, all of which are used as herbicides and are effective in micromolar concentrations.

Anti-microtubule drugs might be applied at various stages of the above methods, such as being incorporated into microspore pretreatment media. The treatment of plants at later developmental stages has the advantage that only already tested haploid regenerants are treated either in vitro (for instance at the shoot culture stage) or in vivo following acclimatization. The concentration and duration of treatments must be always determined in relation to two effects: the percentage of doubled plants and the percentage of survival.

The present invention is applicable to any plant species, whether monocot or dicot. Preferably, plants which may be subject to the methods and uses of the present invention are selected from the group consisting of *Hordeum vulgare, Hordeum bulbusom, Sorghum bicolor, Saccharum officinarium, Zea* spp., including *Zea mays, Setaria italica, Oryza minuta, Oryza sativa, Oryza australiensis, Oryza alta, Triticum aestivum, Triticum durum, Secale cereale*, Triticale, *Malus domestica, Brachypodium distachyon, Hordeum marinum, Aegilops tauschii, Daucus glochidiatus, Beta* spp., including *Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Marus notabilis, Arabidopsis arenosa, Arabidopsis lyrata, Arabidopsis thaliana, Crucihimalaya himalaica, Crucihimalaya wallichii, Cardamine nexuosa, Lepidium virginicum, Capsella bursa pastoris, Olmarabidopsis pumila, Arabis hirsute, Brassica napus, Brassica oleracea, Brassica rapa, Raphanus sativus, Brassica juncacea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Gossypium* sp., *Astragalus sinicus, Lotus japonicas, Torenia fournieri, Allium cepa, Allium fistulosum, Allium sativum, Helianthus annuus, Helianthus tuberosus* and/or *Allium tuberosum*. Particularly preferred are *Beta vulgaris, Zea mays, Triticum aestivum, Hordeum vulgare, Secale cereale, Helianthus annuus, Solanum tuberosum, Sorghum bicolor, Brassica rapa, Brassica napus, Brassica juncacea, Brassica oleracea, Glycine max*, and/or *Gossypium* sp.

Subject-matter of the present invention are also the plants that are obtained or obtainable by the methods described above. Accordingly, one embodiment of the invention is a transgenic plant obtained or obtainable by the above method of transforming a plant cell and regenerating a plant from said cell, as well as progeny or parts thereof, wherein the progeny or the part comprises the at least one nucleotide sequence of interest as transgene. Another embodiment of the invention is a genetically modified plant obtained or obtainable by the above method of modifying the genome of a plant cell and regenerating a plant from said cell as well as progeny or parts thereof, wherein the progeny or the part comprises the modification in the genome introduced by the inventive method. Still a further embodiment of the present invention is a haploid or double haploid plant obtained or obtainable by the above method of producing a haploid plant embryo.

Further subject-matter of the present invention is a plant cell or a seed derived from the above transgenic plant or genetically modified plant. A plant cell derived from the above transgenic plant comprises the at least one nucleotide sequence of interest as transgene while a plant cell derived from the above genetically modified plant comprises the modification in its genome.

Still a further embodiment of the present invention is a plant cell or a seed derived from the above haploid or double haploid plant. The plant cell or seed comprises a haploid or double haploid set of chromosomes.

The invention will be further described with reference to the following Figures and Examples. However, it is to be understood that the invention is not limited to such Examples.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Cray, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

All patents, patent applications, and publications or public disclosures (including publications on internet) referred to or cited herein are incorporated by reference in their entirety.

FIGURES

FIG. 1: shows chemical formula of Hyperphyllin (HP; N-[4-Amino-2-chlorophenyl]-2,4-dichlorobenzamide; CAS #: 42480-64-8) and three different derivatives thereof A1, A2, and A3.

Figure 2:
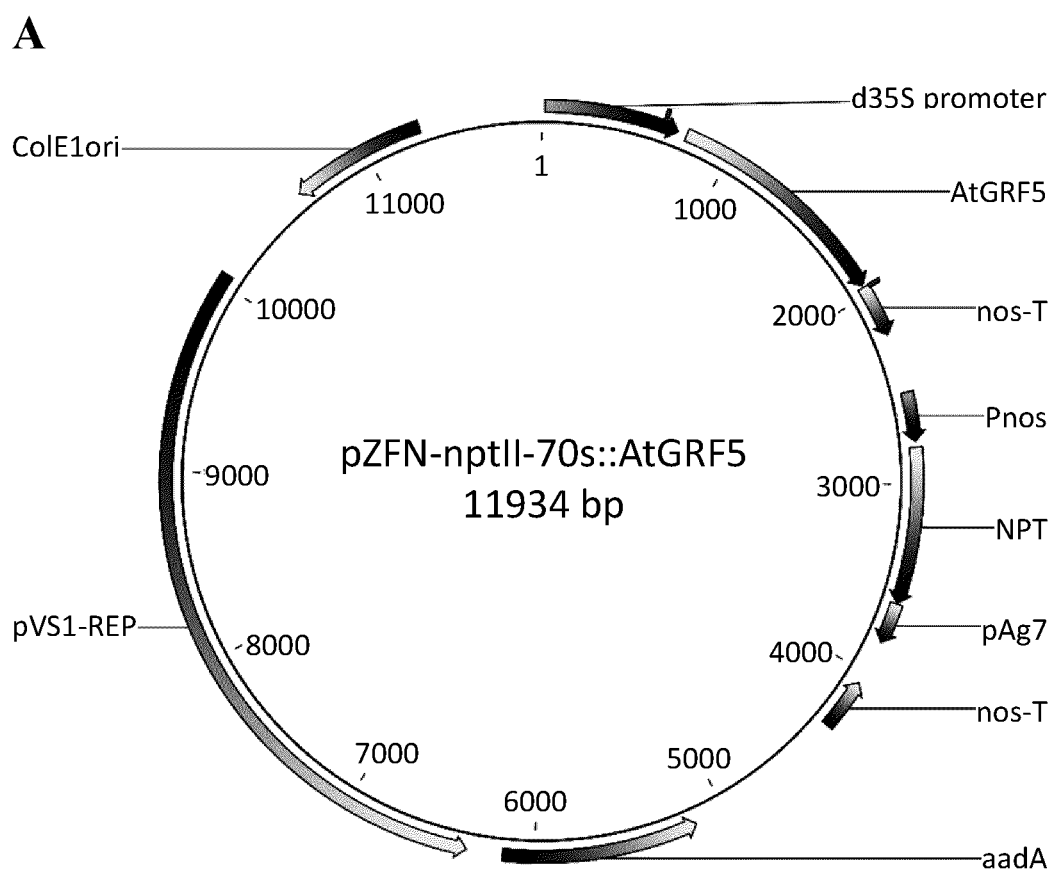
Figure 2:
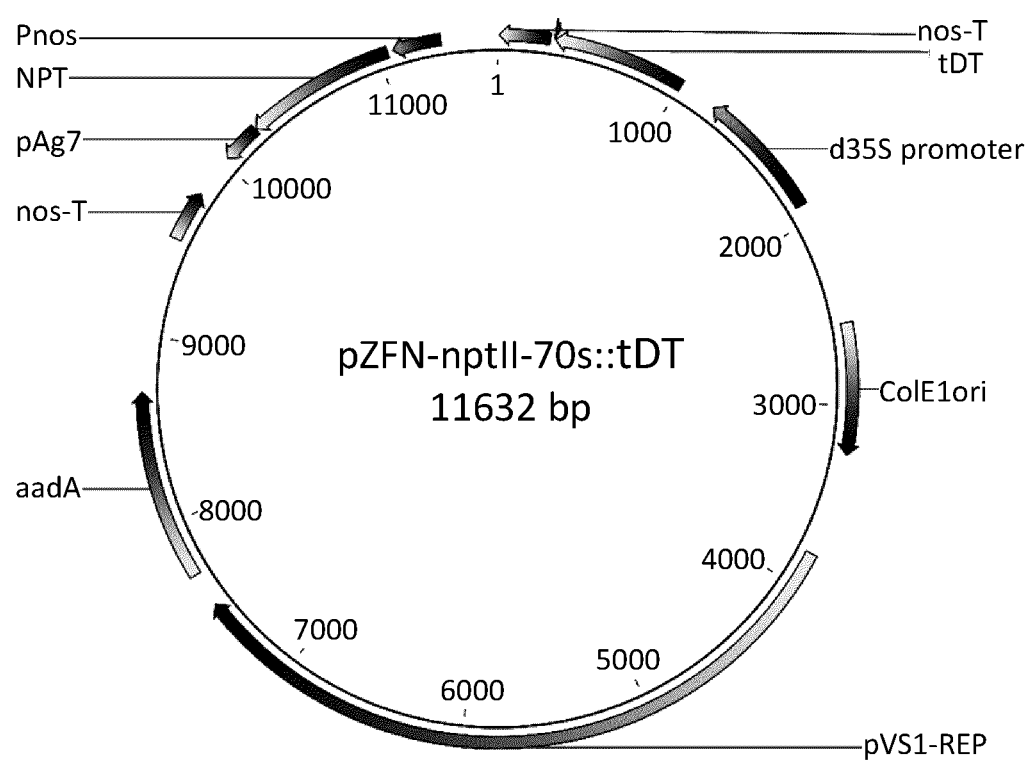

FIG. 2: shows maps of binary vectors pZFN-nptll-70s::AtGRF5 (A) and pZFN-nptll-70s::tDT (B).

Figure 3:
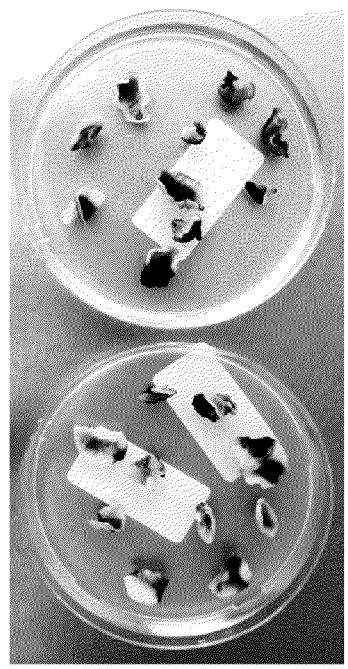
Figure 3:
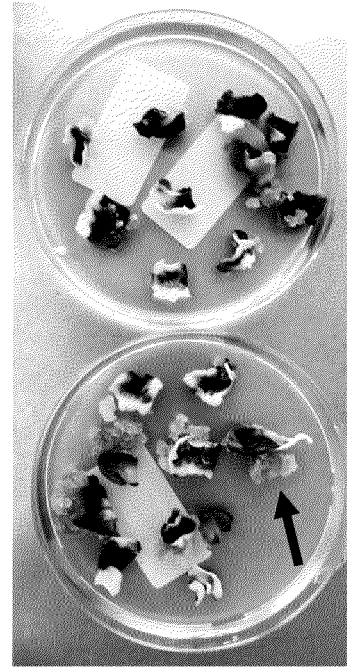
Figure 3:
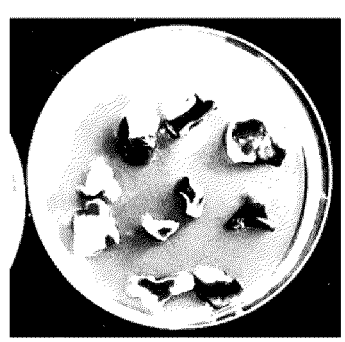
Figure 3:
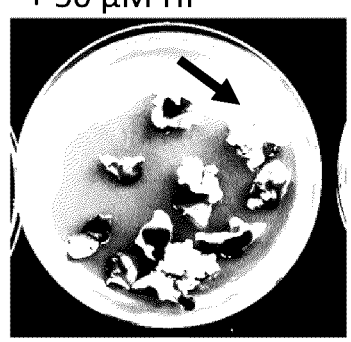

FIG. 3: demonstrates promotion of callus induction in recalcitrant genotype A treated with HP in the concentration of 30 µM and 50 µM. upper panel: 30 µM HP dramatically promotes callus induction in recalcitrant genotype A; lower panel: 50 µM HP has the similar effect but no further increased efficiency. Arrows indicate callus formation. DMSO without HP serves as control.

Figure 4:
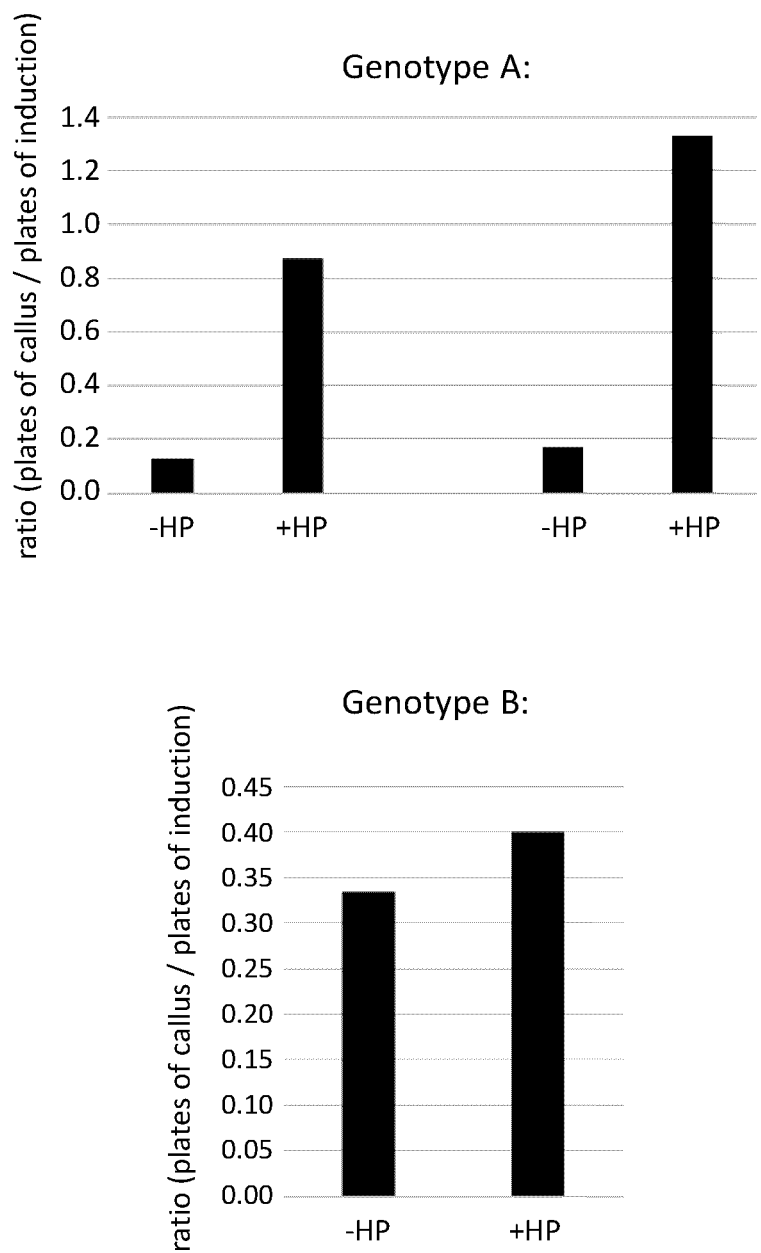

FIG. 4: shows the callus induction efficiency without (−HP) and with HP (+HP) and demonstrates the boosting effect of HP for the recalcitrant genotype A in two repetitions and additional genotype B.

Figure 5:
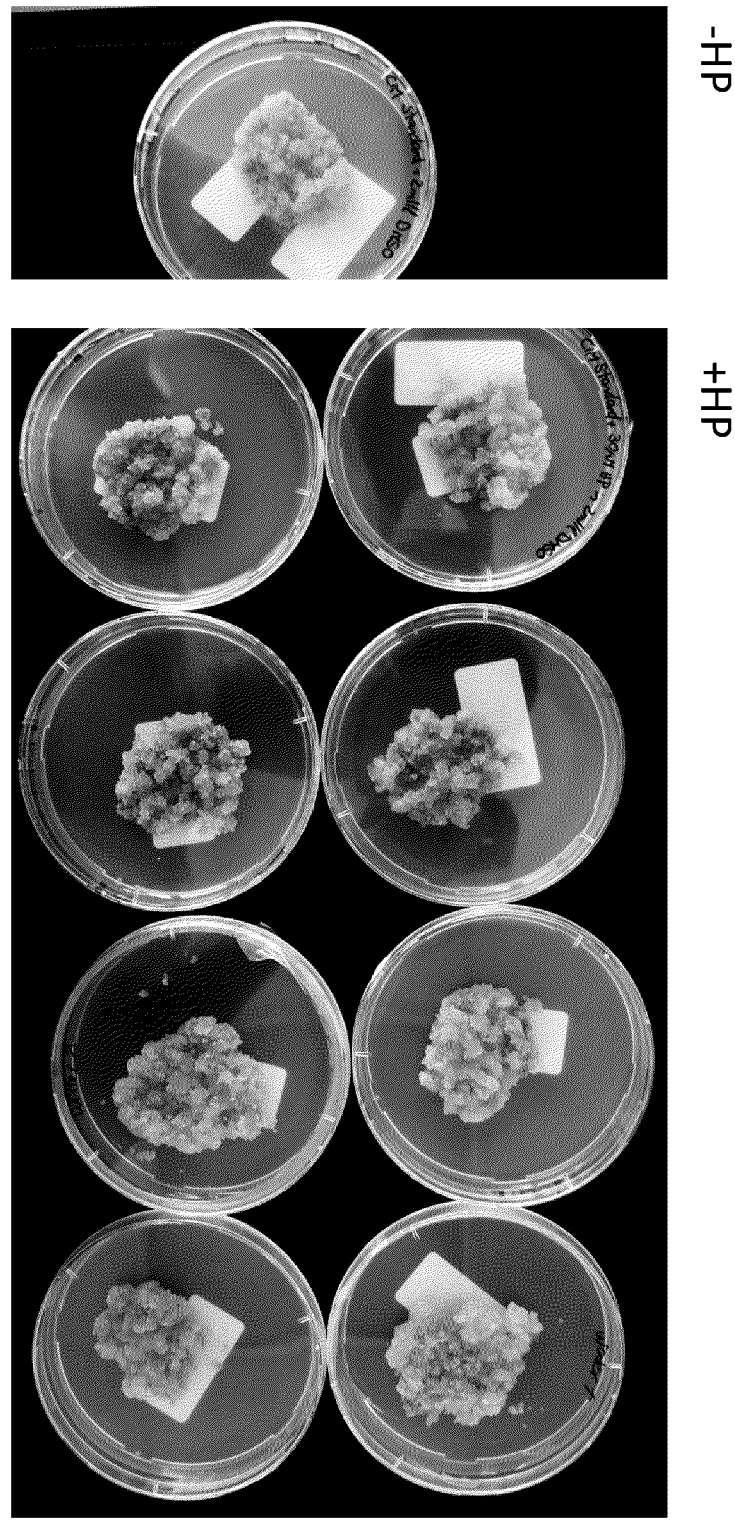

FIG. 5: shows that HP (30 µM)-induced calli (+HP) produce much more amount of callus tissue compared to control without HP (−HP).

Figure 6:

FIG. 6: shows the comparison of plantlets regenerated from calli induced without (−HP) and with HP (+HP). HP-mediated induction results in more regenerated plants from callus.

Figure 7:
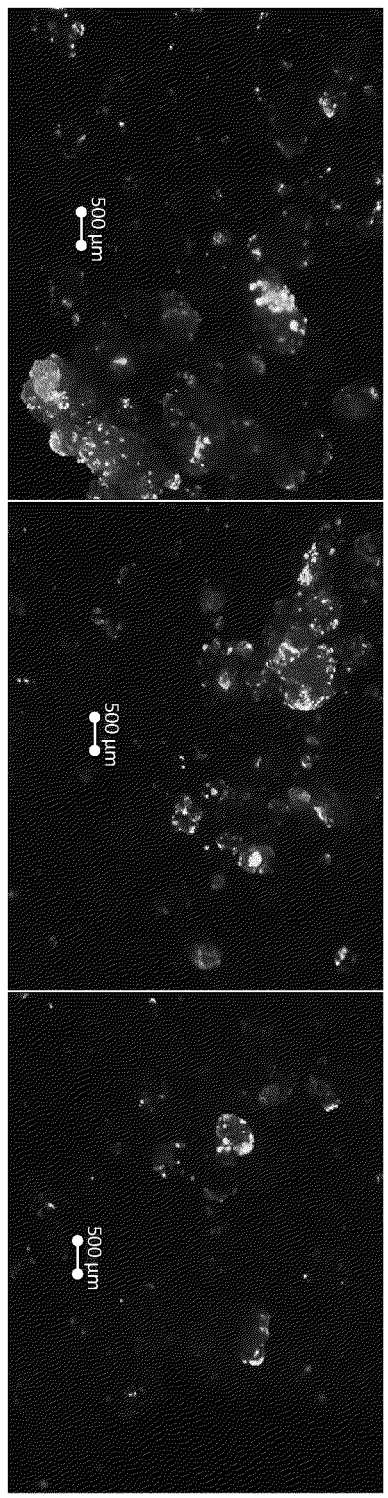
Figure 7:
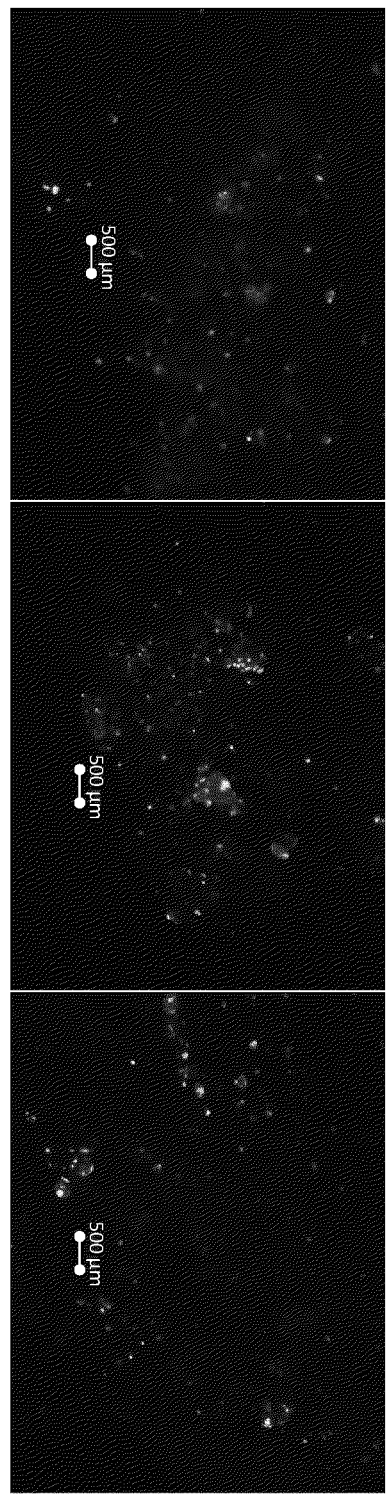

FIG. 7: shows fluorescence imaging of HP induced calli of amenable genotype C and of recalcitrant genotype A seven days after Agrobacteria infection. Both genotypes have been transformed with 70s::tDT construct (see also FIG. 2B). Bright spots and sectors indicate successful *Agrobacterium*-mediated transformation.

Figure 8:
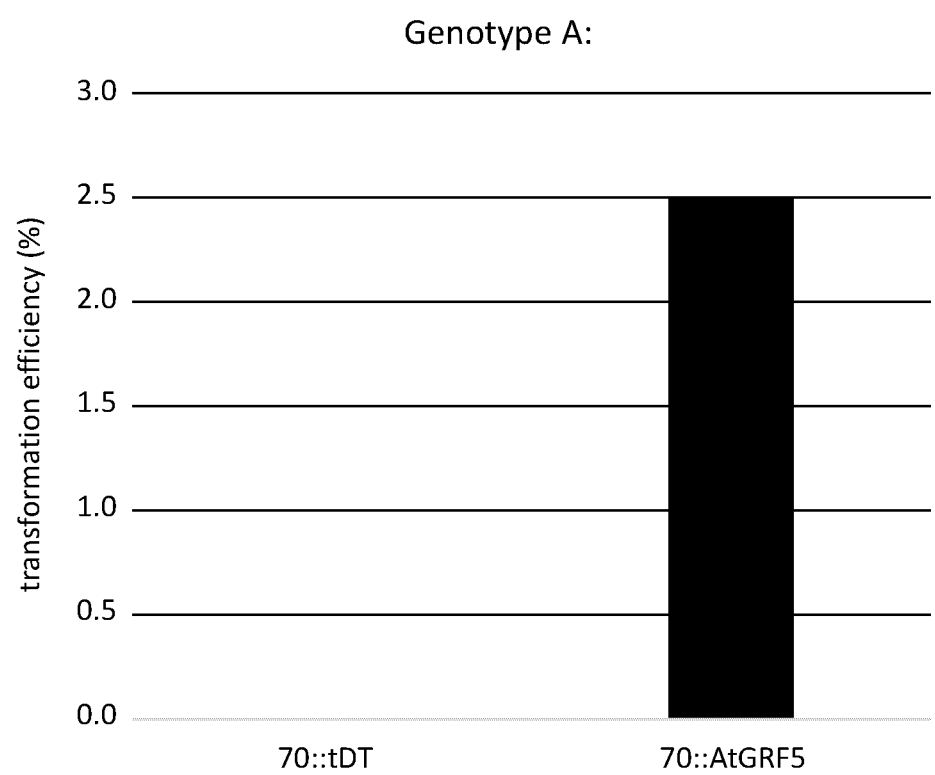

FIG. 8: shows that a HP induced and genetically modified calli of a few recalcitrant genotypes like genotype A could be only regenerated to a whole plant by co-transformation with a regeneration booster gene like AtGRF5.

Figure 9:
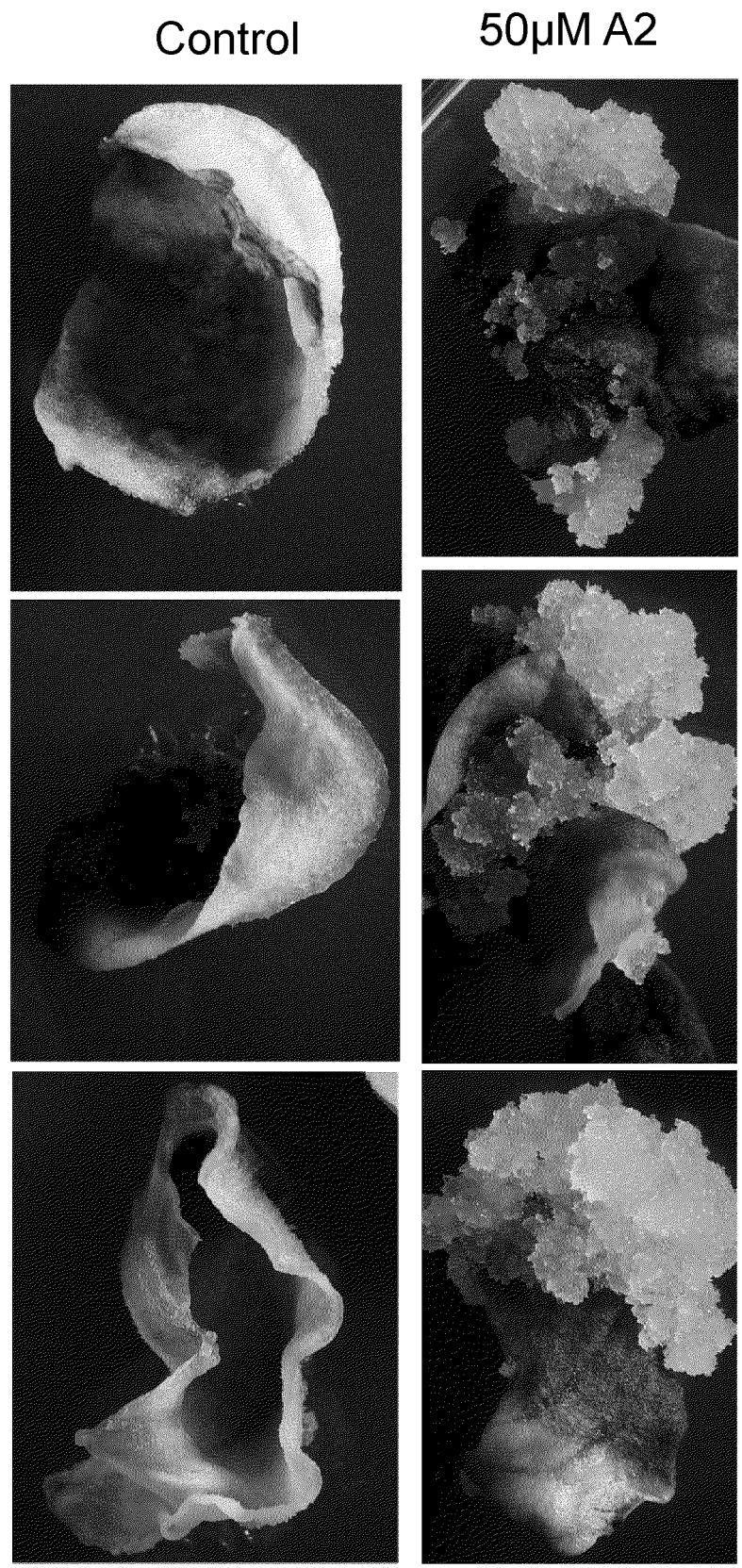

FIG. 9: shows that HP derivate A2 (50 µM) promotes callus induction in recalcitrant genotype (right column). Left column: control without HP treatment.

EXAMPLES

1. Description of the Binary Plasmids

The binary vectors (FIG. 2) pZFN-nptll-70s::AtGRF5 and pZFN-nptll-70s::tDT (both constructs are binary) were produced by following standard cloning procedures. As shown in FIG. 2, within the T-DNA of this vector, the cDNA encoding ArGRF5 (DNA: SEQ ID NO: 1; amino acid: SEQ ID NO: 2) and tDTomato (tDT) as fluorescent marker were cloned between the double CaMV 35S promoter and the terminator of nopaline synthase (NOS) gene. The T-DNA also contains the neomycin phosphotransferase II (nptII) gene that confers resistance to a range of aminoglycoside antibiotics such as kanamycin or paromomycin and was used for the selection of transgenic plant cells and tissues. The NOS promoter and the pAG7 terminator flank the nptII gene. The backbone of the binary vector contains the colE1 and the pVS1 origins for plasmid replication in *Escherichia coli* and *Agrobacterium tumefaciens*, respectively; and the aadA gene that confers streptomycin/spectinomycin resistance for bacteria selection.

Both plasmids were transformed into AGL-1 *Agrobacterium* strain by standard procedure.

2. Sugar Beet Callus Induction

1. Micropropagated shoots of various proprietary genotypes were used as starting material: Genotypes A and B are recalcitrant to callus induction and plant regeneration. For example, genotype A does not show sufficient callus induction and an extremely bad callus quality. Therefore, such calli were never transformable.

Genotype C is less recalcitrant. Shoots were multiplied in MS salts+30 g/l sucrose and 0.25 mg/l benzyladenine (BAP).

2. To induce friable callus, leaf explants were isolated from micropropagated shoots and incubated in callus induction medium (CIM) containing MS salts including 15 g/l sucrose and 2 mg/l BAP at 28° C. for 7 to 8 weeks. To the medium either 2 ml/L DMSO as control, 30 µM HP dissolved in 2 ml/L DMSO or 50 µM HP dissolved in 2 ml/L DMSO has been added. HP is Hyperphyllin, a small molecule with the chemical formula N-[4-Amino-2-chlorophenyl]-2,4-dichlorobenzamide (CAS #: 42480-64-8).

After incubation period the induction and formation of callus has been analysed. FIG. 3 shows that in the recalcitrant genotype A HP in the concentration of 30 µM and 50 µM promotes callus formation. There is no significant difference in induction efficiency between these two concentrations. The quantification of callus induction efficiency with and without HP demonstrates the boosting effect of HP for different recalcitrant genotypes (A and B), even though the increase in efficiency was higher for genotype A (FIG. 4A) than for genotype B (FIG. 4B). After transfer of induced callus on individual plates it has been observed that much more amount of callus tissue could be induced from leaves by application of 30 µM HP compared to control without HP (FIG. 5).

3. Sugar Beet Shoot Induction and Propagation

3. Friable calli of step 2 were harvested from the induction and transferred to the shoot induction medium containing MS salts, 30 g/l sucrose, 1 mg/l GA3 and 1 mg/l Thidiazuron (TDZ). The calli were incubated at 24° C. in the light/dark cycle (16 h/8 h) for 1 to 2 weeks.

4. Regenerated shoots were mounted and cultured in the medium of step 1. The plants are grown at 24° C. in the light/dark cycle (16 h/8 h).

FIG. 6 shows the comparison of plantlets regenerated from calli induced with and without HP. More plants could be regenerated from HP induced callus. All plants induced with HP showed a normal phenotype.

4. Agrobacteria-Mediated Transformation of Sugar Beet Callus a. Sugar beet calli were induced as described in steps 1 and 2.

b. Friable calli were mounted in medium containing MS salts, 30 g/l sucrose, 1 mg/l GA3 and 1 mg/l Thidiazuron (TDZ), and kept for 1 week in the dark, 24° C.

c. *Agrobacterium* AGL-1 harbouring the vector pZFN-nptII-70s::AtGRF5 and pZFN-nptII-70s::tDT was grown in medium (5 g/l tryptone+2.5 g/l yeast extract+1 g/l NaCl+5 g/l mannitol+0.1 g/l MgSO$_4$×7H$_2$O+0.25 g/l KH$_2$PO$_4$+1 g/l glutamic acid, pH 7.0) supplemented with the appropriate antibiotics, at 28° C., for 24 h.

d. Calli were inoculated with *Agrobacterium* suspension (medium: 440 mg/l CaCl$_2$×2H$_2$O+170 mg/l KH$_2$PO$_4$+1.9 g/l KNO$_3$+180.7 mg/l MgSO$_4$+1.65 g/l NH$_4$NO$_3$+2 mg/l BAP+ 40 µg/l Acetosyringone+20 g/l sucrose+2 g/l glucose, pH 6.0) at an OD600 of 0.8. The callus tissue and the *Agrobacterium* were incubated in medium comprising 440 mg/l CaCl$_2$×2H$_2$O, 170 mg/l KH$_2$PO$_4$, 1.9 g/l KNO$_3$, 180.7 mg/l MgSO$_4$, 1.65 g/l NH$_4$NO$_3$, 2 mg/l BAP, 40 µg/l Acetosyringone, 20 g/l sucrose and 2 g/l glucose, at 21° C. for 3 days in the dark.

e. Calli were sub-cultured to medium comprising MS salts, 30 g/l sucrose, 1 mg/l GA3, 1 mg/l TDZ and 500 mg/l Timentin, and incubated in the dark, at 24° C. for 1 week.

f. To select the transgenic calli, samples were transferred to medium containing MS salts, 30 g/l sucrose, 1 mg/l GA3, 1 mg/l TDZ, 500 mg/l Timentin and 100 mg/l Paromomycin, and incubated at 24° C. in the light/dark cycle (16 h/8 h) for 3 weeks.

g. Transgenic calli were selected and sub-cultured for several times in the same medium and conditions.

h. Regenerating shoots were isolated and propagated in medium containing MS salts, 30 g/l sucrose, 0.25 mg/l benzyladenine (BAP) and 100 mg/l kanamycin.

i. Leaf explants were isolated from the green growing shoots for DNA extraction and PCR analysis, in order to confirm the putative transgenic lines.

j. Selected shoots were rooted in medium (MS salts+30 g/l sucrose+6.25 mg/l NAA) and transferred to the green house for seed production.

FIG. 7 shows that HP induced callus from recalcitrant genotype can be infected by agrobacteria. Nevertheless, the regeneration of transgenic plants from calli of recalcitrant genotypes was not always possible. Transgenic plants could be obtained from HP induced callus often only by additional expression of a regeneration booster gene like AtGRF5 (see PCT/EP2018/086902) (FIG. 8).

Additionally, different concentrations (10, 30, 50, 100, 500 μM, and 1 mM) of HP has been tested according the above described process. Only 30 and 50 μM showed a strong callus inducing effect. However, 10 and 100 μM caused at least a modest effect, whereby higher concentration showed no effect (Table 1). Further, also HP derivates A1 and A2 have been tested in concentrations of 30 and 50 μM. Derivate A2 led to strong callus-inducing effect at 30 μM (FIG. 9) and only a weak effect at 50 μM. Derivate A1 worked only at a concentration of 30 μM (Table 1).

Table 1: Test of different HP derivates in different concentrations ("−": no callus induction effect; "+": modest callus induction effect; "++": strong callus induction effect)

TABLE 1

Test of different HP derivates in different concentrations

| Chemical compound | Concentration (dissolved in 2 ml/L DMSO) | Callus induction effect |
|---|---|---|
| HP | 10 μM | + |
| HP | 30 μM | ++ |
| HP | 50 μM | ++ |
| HP | 100 μM | + |
| HP | 500 μM | − |
| HP | 1 mM | − |
| HP derivate A1 | 30 μM | + |
| HP derivate A1 | 50 μM | − |
| HP derivate A2 | 30 μM | ++ |
| HP derivate A2 | 50 μM | + |

(−: no callus induction effect; +: modest callus induction effect; ++: strong callus induction effect)

The invention claimed is:

1. A method for inducing callus formation from sugar beet plant cells, comprising incubating the sugar beet plant cells in the presence of hyperphyllin or a derivative thereof selected from the group consisting of

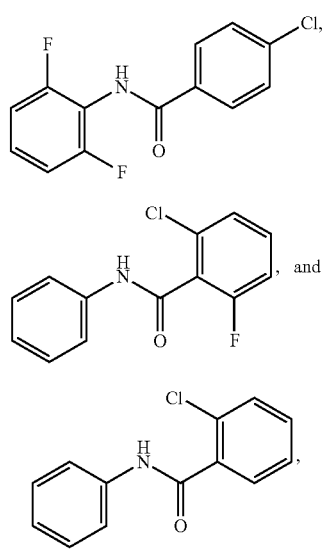

combinations thereof.

2. The method of claim 1, wherein the sugar beet plant cells are incubated in a culture medium comprising the hyperphyllin or the derivative thereof and/or wherein the hyperphyllin or the derivative thereof is introduced into the sugar beet plant cells.

3. A method for producing sugar beet plant shoots, comprising
   (i) inducing callus formation according to the method of claim 1 to yield sugar beet callus tissue, and
   (ii) cultivating the callus tissue under conditions suitable to induce sugar beet shoot formation.

4. A method for producing a transgenic sugar beet plant, comprising the following steps:
   (a) inducing callus formation according to the method of claim 1 to yield sugar beet callus tissue,
   (b) introducing into a sugar beet plant cell to be used in step (a) and/or into a cell of the sugar beet callus tissue obtained in step (a) at least one nucleotide sequence of interest or at least one polypeptide of interest,
   (c) cultivating the sugar beet callus tissue obtained from steps (a) and (b) under conditions suitable to induce shoot formation to yield sugar beet plant shoots, and
   (d) regenerating a transgenic sugar beet plant.

5. A method of producing a genetically modified sugar beet plant, comprising the following steps:
   (a) inducing callus formation according to the method of claim 1 to yield sugar beet callus tissue, and
   (b) modifying the genome of a sugar beet plant cell to be used in step (a) and/or of a cell of the sugar beet callus tissue obtained in step (a) by introducing into said cell a single stranded DNA break (SSB) inducing enzyme or a double stranded DNA break (DSB) inducing enzyme which recognizes a predetermined site in the genome of said cell, and optionally a repair nucleic acid molecule, and/or a base editor fused to a catalytically impaired SSB or DSB inducing enzyme or fused to a SSB inducing enzyme which recognizes a predetermined site in the genome of said cell,
   wherein the modification of said genome is selected from
   i. a replacement of at least one nucleotide;
   ii. a deletion of at least one nucleotide;
   iii. an insertion of at least one nucleotide; or
   iv. any combination of i.-iii.,
   (c) cultivating the sugar beet callus tissue obtained from steps (a) and (b) under conditions suitable to induce shoot formation to yield sugar beet plant shoots, and
   (d) regenerating a genetically modified sugar beet plant.

6. A method of producing a haploid or double haploid sugar beet plant, comprising the steps
   (a) inducing callus formation from an immature male gametophyte or a microspore according to the method of claim 1 to yield sugar beet callus tissue,
   (b) cultivating the sugar beet callus tissue obtained in step (a) under conditions suitable to induce shoot formation to yield sugar beet plant shoots,
   (c) optionally conducting chromosome doubling, and
   (d) regenerating a haploid or double haploid sugar beet plant.

7. A transgenic sugar beet plant obtained by the method of claim 4 or a progeny plant thereof.

8. A genetically modified sugar beet plant obtained by the method of claim 5, or a progeny plant thereof.

9. A haploid or double haploid sugar beet plant obtained by the method of claim 6 or a progeny plant thereof.

10. A sugar beet plant cell or a seed of the sugar beet plant of claim 7, wherein the sugar beet plant cell or the seed comprises the at least one introduced nucleotide sequence of interest or the at least one polypeptide of interest as a transgene.

11. A sugar beet plant cell or a seed of the sugar beet plant of claim 8, wherein the sugar beet plant cell or the seed comprises the modification in the genome.

12. A sugar beet plant cell or a seed of the sugar beet plant of claim 9, wherein the plant cell or the seed comprises a haploid or double haploid set of chromosomes.

13. A method of using hyperphyllin or a derivative thereof selected from the group consisting of formula A1, A2 or A3, in a method for inducing callus formation from sugar beet plant cells or in a method for indirect regeneration of a sugar beet plant,
   wherein the hyperphyllin derivatives have the following structures:

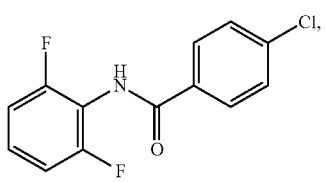

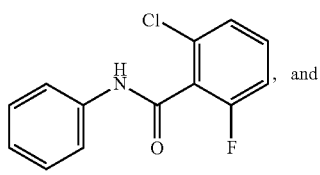 A2

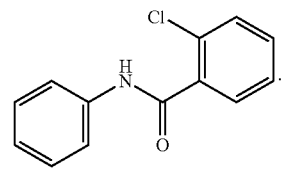 A3

14. A method of using hyperphyllin or a derivative thereof selected from the group consisting of formula A1, A2 or A3, in a method for production of a transgenic sugar beet plant cell, plant or seed, in a method for production of a genetically modified sugar beet plant cell, plant or seed or in a method for production of a haploid or double haploid sugar beet plant cell, plant or seed, wherein the hyperphyllin derivatives have the following structures:

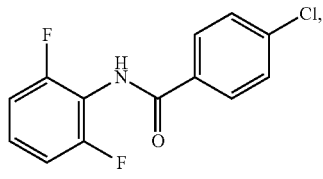 A1

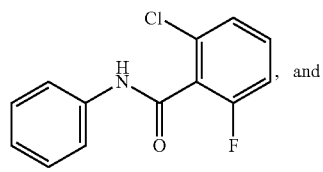 A2

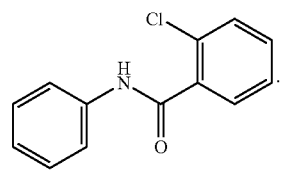 A3

* * * * *